United States Patent
Wilder et al.

(10) Patent No.: US 10,897,978 B2
(45) Date of Patent: *Jan. 26, 2021

(54) METHOD OF IMPROVING SKIN APPEARANCE

(71) Applicant: The Procter & Gamble Company, Cincinnati, OH (US)

(72) Inventors: Elizabeth Anne Wilder, West Chester, OH (US); Paul Jonathan Matts, Addlestone (GB); Nicole Annette Mosby, Cincinnati, OH (US); Colin John Clarke, Ashford (GB)

(73) Assignee: The Procter & Gamble Company, Cincinnati, OH (US)

( * ) Notice: Subject to any disclaimer, the term of this patent is extended or adjusted under 35 U.S.C. 154(b) by 245 days.

This patent is subject to a terminal disclaimer.

(21) Appl. No.: 14/918,989

(22) Filed: Oct. 21, 2015

(65) Prior Publication Data

US 2016/0107004 A1 Apr. 21, 2016

Related U.S. Application Data

(60) Provisional application No. 62/066,765, filed on Oct. 21, 2014.

(51) Int. Cl.
*A61Q 19/00* (2006.01)
*A61M 35/00* (2006.01)
(Continued)

(52) U.S. Cl.
CPC .......... *A45D 44/002* (2013.01); *A45D 33/38* (2013.01); *A45D 37/00* (2013.01); *A45D 40/18* (2013.01); *A45D 40/24* (2013.01); *A61K 8/0208* (2013.01); *A61K 8/36* (2013.01); *A61K 8/361* (2013.01); *A61K 8/38* (2013.01); *A61K 8/64* (2013.01);
(Continued)

(58) Field of Classification Search
None
See application file for complete search history.

(56) References Cited

U.S. PATENT DOCUMENTS

| 4,341,209 A | 7/1982 | Schaar |
| 4,699,792 A | 10/1987 | Nick et al. |

(Continued)

FOREIGN PATENT DOCUMENTS

| EP | 2 559 425 A1 | 2/2013 |
| JP | 2002-249422 A | 9/2002 |

(Continued)

OTHER PUBLICATIONS

English translation of JP 2009273674 A (Year: 2009).*

(Continued)

*Primary Examiner* — Nicole P Babson
(74) *Attorney, Agent, or Firm* — John G. Powell

(57) ABSTRACT

Disclosed are composition and methods for treating skin whereby a cosmetic composition is applied to a target area of skin. The cosmetic composition comprises an effective amount of a skin active agent. A barrier patch is also provided and has a backing layer and a pressure sensitive adhesive. The barrier patch has an adhesive release force of about 50 gms to about 400 gms; a WVTR from about 1 $g/m^2/24$ h to about 500 $g/m^2/24$ h; and a flexibility from about 8 grams to about 40 grams.

19 Claims, 5 Drawing Sheets

(51) Int. Cl.
| | |
|---|---|
| *A61K 8/49* | (2006.01) |
| *A61K 8/34* | (2006.01) |
| *A61K 8/42* | (2006.01) |
| *A61Q 19/08* | (2006.01) |
| *A61M 37/00* | (2006.01) |
| *A61K 8/06* | (2006.01) |
| *A45D 44/00* | (2006.01) |
| *A45D 33/38* | (2006.01) |
| *A45D 37/00* | (2006.01) |
| *A45D 40/24* | (2006.01) |
| *A61K 8/02* | (2006.01) |
| *B65D 5/489* | (2006.01) |
| *B65D 5/68* | (2006.01) |
| *B65D 5/66* | (2006.01) |
| *A45D 40/18* | (2006.01) |
| *A61K 8/36* | (2006.01) |
| *A61K 8/38* | (2006.01) |
| *A61K 8/64* | (2006.01) |
| *A61K 8/67* | (2006.01) |
| *B65D 77/00* | (2006.01) |
| *B65D 77/30* | (2006.01) |
| *A61F 13/00* | (2006.01) |

(52) U.S. Cl.
CPC .............. *A61K 8/671* (2013.01); *A61K 8/673* (2013.01); *A61K 8/678* (2013.01); *A61Q 19/00* (2013.01); *B65D 5/4802* (2013.01); *B65D 5/66* (2013.01); *B65D 5/68* (2013.01); *B65D 77/006* (2013.01); *B65D 77/30* (2013.01); *A45D 2200/053* (2013.01); *A45D 2200/1036* (2013.01); *A61F 13/00063* (2013.01); *A61K 2800/10* (2013.01); *A61K 2800/87* (2013.01); *A61K 2800/88* (2013.01); *A61M 35/10* (2019.05); *B65D 2203/00* (2013.01)

(56) References Cited

U.S. PATENT DOCUMENTS

| | | | |
|---|---|---|---|
| 4,711,781 | A | 12/1987 | Nick et al. |
| 4,725,439 | A | 2/1988 | Campbell et al. |
| 4,743,249 | A | 5/1988 | Loveland |
| 4,773,408 | A | 9/1988 | Cilento et al. |
| 5,051,259 | A | 9/1991 | Olsen et al. |
| 5,123,900 | A | 6/1992 | Wick |
| 5,132,115 | A | 7/1992 | Wolter et al. |
| 5,262,165 | A | 11/1993 | Govil et al. |
| 5,387,450 | A | 2/1995 | Stewart |
| 5,455,043 | A | 10/1995 | Fischel-Ghodsian |
| 5,476,664 | A | 12/1995 | Robinson et al. |
| 5,503,844 | A | 4/1996 | Kwiatek et al. |
| 5,629,014 | A | 5/1997 | Kwiatek et al. |
| 5,641,506 | A | 6/1997 | Talke et al. |
| 5,713,842 | A | 2/1998 | Kay |
| 5,723,138 | A | 3/1998 | Bae et al. |
| 5,785,978 | A | 7/1998 | Porter et al. |
| 5,820,877 | A | 10/1998 | Yamaguchi et al. |
| 5,958,447 | A | 9/1999 | Haralambopoulos et al. |
| 5,965,154 | A | 10/1999 | Haralambopoulos |
| 5,968,533 | A | 10/1999 | Porter et al. |
| 6,162,458 | A | 12/2000 | Asada et al. |
| 6,168,028 | B1 | 1/2001 | Telesca et al. |
| 6,200,596 | B1 | 3/2001 | Schwartzmiller et al. |
| 6,221,369 | B1 | 4/2001 | Pool et al. |
| 6,277,401 | B1 | 8/2001 | Bello et al. |
| 6,325,565 | B1 | 12/2001 | Girardot et al. |
| 6,338,855 | B1 | 1/2002 | Albacarys et al. |
| 6,448,303 | B1 | 9/2002 | Paul |
| 6,495,158 | B1 | 12/2002 | Buseman et al. |
| 6,495,229 | B1 | 12/2002 | Carte et al. |
| 6,673,363 | B2 | 1/2004 | Luo et al. |
| 6,676,962 | B1 | 1/2004 | Muller |
| 6,730,317 | B2 | 5/2004 | Gueret |
| 6,899,840 | B2 | 5/2005 | Ueda et al. |
| 6,926,960 | B1 | 8/2005 | Hoshino et al. |
| 6,953,602 | B2 | 10/2005 | Carte et al. |
| 7,063,859 | B1 | 6/2006 | Kanios et al. |
| 7,256,234 | B2 | 8/2007 | Nierle et al. |
| 7,531,185 | B2 | 5/2009 | Chen et al. |
| 7,658,942 | B2 | 2/2010 | Deckner et al. |
| 7,854,938 | B2 | 12/2010 | Ueda et al. |
| 8,728,514 | B2 | 5/2014 | Choi et al. |
| 9,066,888 | B2 | 6/2015 | Kugelmann et al. |
| 2002/0187181 | A1 | 12/2002 | Godbey et al. |
| 2003/0072724 | A1 | 4/2003 | Maibach et al. |
| 2003/0082219 | A1 | 5/2003 | Warren et al. |
| 2003/0152610 | A1 | 8/2003 | Rolf et al. |
| 2003/0167556 | A1 | 9/2003 | Kelley |
| 2003/0175328 | A1 | 9/2003 | Shefer et al. |
| 2003/0180347 | A1 | 9/2003 | Young et al. |
| 2004/0009202 | A1 | 1/2004 | Woller |
| 2004/0116018 | A1 | 6/2004 | Fenwick et al. |
| 2004/0202706 | A1 | 10/2004 | Koo et al. |
| 2005/0013784 | A1 | 1/2005 | Trigg et al. |
| 2005/0266059 | A1 | 12/2005 | Poss |
| 2006/0104931 | A1 | 5/2006 | Fukutome et al. |
| 2006/0121097 | A1 | 6/2006 | Lodge et al. |
| 2006/0177487 | A1* | 8/2006 | Martz ................ A61K 8/0208 424/443 |
| 2006/0198879 | A1 | 9/2006 | Fukuta et al. |
| 2007/0020220 | A1 | 1/2007 | Osborne |
| 2007/0060855 | A1 | 3/2007 | Leung et al. |
| 2007/0254021 | A1 | 11/2007 | Scimeca et al. |
| 2007/0292491 | A1 | 12/2007 | Hansen et al. |
| 2007/0298089 | A1 | 12/2007 | Saeki et al. |
| 2008/0014231 | A1 | 1/2008 | Okano |
| 2008/0138593 | A1 | 6/2008 | Martinez |
| 2008/0260808 | A1 | 10/2008 | Pinna et al. |
| 2009/0010998 | A1 | 1/2009 | Marchitto et al. |
| 2009/0155326 | A1 | 6/2009 | Mack et al. |
| 2009/0234308 | A1 | 9/2009 | Jackson et al. |
| 2009/0249558 | A1 | 10/2009 | Fileccia et al. |
| 2009/0258062 | A1 | 10/2009 | Horstmann |
| 2010/0239619 | A1 | 9/2010 | Hurwitz |
| 2011/0200652 | A1 | 8/2011 | Smith et al. |
| 2011/0300198 | A1 | 12/2011 | Nussinovitch et al. |
| 2012/0308619 | A1 | 12/2012 | Tousley |
| 2013/0042417 | A1 | 2/2013 | Smith et al. |
| 2013/0178407 | A1 | 7/2013 | Fileccia et al. |
| 2014/0083878 | A1 | 3/2014 | Tang et al. |
| 2014/0276478 | A1 | 9/2014 | Liao et al. |
| 2014/0377512 | A1 | 12/2014 | Rogers et al. |
| 2015/0209243 | A1 | 7/2015 | Shiroya et al. |
| 2015/0320606 | A1 | 11/2015 | Kawahara |
| 2017/0112724 | A1 | 4/2017 | Boswell et al. |
| 2017/0112725 | A1 | 4/2017 | Boswell et al. |
| 2017/0112726 | A1 | 4/2017 | Boswell et al. |
| 2017/0112727 | A1 | 4/2017 | Boswell et al. |
| 2018/0098921 | A1 | 4/2018 | Boswell et al. |
| 2018/0193229 | A1 | 7/2018 | Boswell et al. |
| 2018/0193230 | A1 | 7/2018 | Boswell et al. |
| 2018/0200158 | A1 | 7/2018 | Boswell et al. |
| 2018/0360698 | A1 | 12/2018 | Boswell |
| 2018/0369079 | A1 | 12/2018 | Boswell |

FOREIGN PATENT DOCUMENTS

| | | | |
|---|---|---|---|
| JP | 2004-51516 A | | 2/2004 |
| JP | 2006021789 | | 1/2006 |
| JP | 2009273674 A | * | 11/2009 |
| JP | 2011-178693 A | | 9/2011 |
| KR | 2008-0014461 A | | 2/2008 |
| KR | 10-0871282 B1 | | 11/2008 |
| WO | 95/28136 A1 | | 10/1995 |
| WO | 97/32567 A1 | | 9/1997 |
| WO | 97/48387 A1 | | 12/1997 |
| WO | 99/26572 A1 | | 6/1999 |
| WO | 03/063817 A1 | | 8/2003 |
| WO | 03/084579 A1 | | 10/2003 |
| WO | 2004/077990 A1 | | 9/2004 |

(56) References Cited

FOREIGN PATENT DOCUMENTS

| WO | 2004/078122 | A2 | 9/2004 |
|----|-------------|----|--------|
| WO | 2006/062740 | A2 | 6/2006 |
| WO | 2008/071310 | A1 | 6/2008 |
| WO | 2009/055048 | A1 | 4/2009 |

OTHER PUBLICATIONS

U.S. Appl. No. 14/919,048, filed Oct. 21, 2015, Elizabeth Anne Wilder et al.
International Search Report and Written Opinion of the International Searching Authority, PCT/US2015/056670, dated Dec. 21, 2015, 16 pages.
Savlon Day Out First Aid Kit, Mintel's GNPD Database Record ID: 1119887, Jun. 2009, 2 pages.
International Search Report and Written Opinion of the International Searching Authority, PCT/US2015/056667, dated Dec. 21, 2015, 13 pages.
U.S. Appl. No. 16/358,225, filed Mar. 19, 2019, Emily Charlotte Boswell et al.
All Office Actions, U.S. Appl. No. 14/919,048.
All Office Actions, U.S. Appl. No. 16/015,644.
All Office Actions, U.S. Appl. No. 16/358,225.
All Office Actions, U.S. Appl. No. 15/296,630.
All Office Actions, U.S. Appl. No. 15/296,713.
All Office Actions, U.S. Appl. No. 15/296,736.
All Office Actions, U.S. Appl. No. 15/839,287.
All Office Actions, U.S. Appl. No. 15/843,812.
All Office Actions, U.S. Appl. No. 15/843,866.
All Office Actions, U.S. Appl. No. 15/865,384.
All Office Actions, U.S. Appl. No. 15/865,402.
All Office Actions, U.S. Appl. No. 15/296,768.
International Search Report and Written Opinion of the International Searching Authority, PCT/US2016/057470, dated Dec. 20, 2016, 10 pages.
International Search Report and Written Opinion of the International Searching Authority, PCT/US2016/057472, dated Dec. 23, 2016, 12 pages.
International Search Report and Written Opinion of the International Searching Authority, PCT/US2018/012869, dated Apr. 30, 2018, 12 pages.
International Search Report and Written Opinion of the International Searching Authority, PCT/US2018/012870, dated Apr. 30, 2018, 13 pages.
International Search Report and Written Opinion of the International Searching Authority, PCT/US2018/012871, dated May 28, 2018, 10 pages.
International Search Report and Written Opinion of the International Searching Authority, PCT/US2018/012873, dated May 28, 2018, 10 pages.
International Search Report and Written Opinion of the International Searching Authority, PCT/US2018/038896, dated Oct. 5, 2018, 10 pages.
PCT International Search Report, dated Dec. 20, 2016, 10 pages.

\* cited by examiner

METHOD OF IMPROVING SKIN APPEARANCE

TECHNICAL FIELD

The present invention relates to method of delivering cosmetic compositions to a target area of the skin via the use of a barrier patch. The barrier patch comprises a backing layer and a pressure sensitive adhesive. The barrier patch has improved properties that provide greater comfort in use, long lasting adhesion, ease of removal, more efficient delivery of skin care agents to the skin, and that affords greater formulation flexibility.

BACKGROUND OF THE INVENTION

The benefits of using a patch or mask device comprising skin agents to cosmetically treat the skin, have been recognized in the art. A variety of cosmetic patches or devices are commercially marketed or described as being useful for the delivery of skin actives. Patches have also been described in the literature and marketed in the medical field as a useful means for the transdermal administration of drugs.

However, many patches or devices suffer drawbacks in their physical product forms resulting in undesirable in-use characteristics as perceived by the wearer. For example, some patches are too wet or sticky. A patch or device that comprises gel forming agents may not form a solid gel structure and as a result, are difficult to handle and apply to the skin. Other patches are dry, rough, and inflexible and thus are tight and uncomfortable to wear. These patches often do not conform well to the contours of the skin surface to which they are applied. Some patches or devices are too flexible. These patches are thus difficult to handle and apply and may actually conform too closely to the contours of the skin emphasizing wrinkles or even inducing wrinkles. Some patches and devices are difficult to remove due to the use of strong adhesives. They may leave behind residue after removal due to their high adhesive and/or cohesive properties.

Moreover, patches and devices are also known where the active agents are incorporated into the adhesive materials in the patch. Thus these patches serve as a delivery substrate for the actives. Incompatibility between the skin agents and the adhesive materials may result in ineffective partitioning of the skin agents through the adhesive layer. This leads to inferior penetration of the skin agents into the layers of the skin. Thus some patches or devices do not provide an effective release and penetration of skin care benefit agents.

It has now been found that a user's satisfaction may be improved by rebalancing the properties of the barrier patch. By selecting the proper degree of flexibility, adhesive strength for ease of removal, occlusion and permeability, skin active agents are effectively delivered to the skin, and a superior and comfortable in use experience is provided for the consumer. Furthermore, embodiments herein allow greater formulation flexibility, for example, by allowing the incorporation of a broader range of skin active agents, which would otherwise interact with the adhesive material.

SUMMARY OF THE INVENTION

In accordance with one embodiment, a method of treating skin is provided comprising:
a. applying a cosmetic composition to a target area of the skin, comprising an effective amount of a skin active agent, in an embodiment the skin active agent is provided as a separate component from a barrier patch;
b. applying the barrier patch to the target area of skin, the barrier patch comprising a backing layer having a first surface; a pressure sensitive adhesive in contact with the first surface; adjusting the properties of the barrier patch to have: an adhesive release force of about 50 gms to about 400 gms; a WVTR from about 1 $g/m^2/24$ h to about 500 $g/m^2/24$ h; in another embodiment from about 1 $g/m^2/24$ h to about 180 $g/m^2/24$ h and a flexibility from about 8 grams to about 40 grams.

In an embodiment the cosmetic composition is maintained in contact with the target area of skin via the barrier patch, for a period of time from about 2 hours to about 1 week and/or from about 2 hours to about 12 hours.

In accordance with another embodiment, a method of treating skin is provided comprising:
a. applying a cosmetic composition to a target area of the skin, comprising an oil in water emulsion with an effective amount of a skin active agent that is provided as separate component from a barrier patch;
b. applying the barrier patch comprising:
 a backing layer having a first surface;
 a pressure sensitive adhesive in contact with the first surface;
 adjusting the properties of the barrier patch to have:
 an adhesive release of from about 75 gms to about 350 gms;
 a WVTR from about 1 $g/m^2/24$ h to about 180 $g/m^2/24$ h;
 a flexibility from about 8 grams to about 25 grams.

In accordance with another embodiment, a method of treating skin is provided comprising:
a. applying a cosmetic composition to a target area of the skin, comprising an effective amount of a skin active agent that is provided as separate component from a barrier patch;
b. applying the barrier patch comprising:
 a backing layer having a first surface;
 a pressure sensitive adhesive in contact with the first surface;
 adjusting the properties of the barrier patch to have:
 an adhesive release force of about 50 gms to about 400 gms;
 a WVTR from about 1 $g/m^2/24$ h to about 500 $g/m^2/24$ h;
 a flexibility from about 8 grams to about 40 grams; and
adjusting the barrier patch to provide a hydration value of about 35 to about 120.

In further embodiments, a skin care kit is provided comprising:
a cosmetic composition comprising an effective amount of a skin active agent;
a barrier patch comprising a backing layer having a first surface and a pressure sensitive adhesive in contact with the first surface; the barrier patch comprising an adhesive release force of from about 50 gms to about 400 gms; a flexibility from about 8 grams to about 40 grams; and a WVTR from about 1 $g/m^2/24$ h to about 500 $g/m^2/24$ h;
a display package comprising:
 a display surface or an inclined display surface. defining a first cavity to contain the cosmetic composition and a second cavity to contain a plurality of barrier patches.

In another embodiment the display package further comprises a top cover having a front wall, a back wall and two sidewalls; a base having a front wall, a back wall and two sidewalls; an intermediate surround window positioned between said top cover and said base. The cosmetic composition may either be positioned substantially within the first cavity or positioned in an upright position in the first cavity. The edges of the front wall, back wall and two sidewalls of the top cover may be configured to mate with the edges of the front wall, back wall and two sidewalls of the base when the intermediate surround window is removed to provide a close fitting relationship.

The cosmetic compositions in any of the embodiments of this summary may comprise an aqueous cosmetic composition.

BRIEF DESCRIPTION OF THE DRAWINGS

While the specification concludes with claims that particularly point out and distinctly claim the invention, it is believed that the present invention will be better understood from the following description of embodiments, taken in conjunction with the accompanying drawings in which:

DETAILED DESCRIPTION OF THE INVENTION

Figure 1:
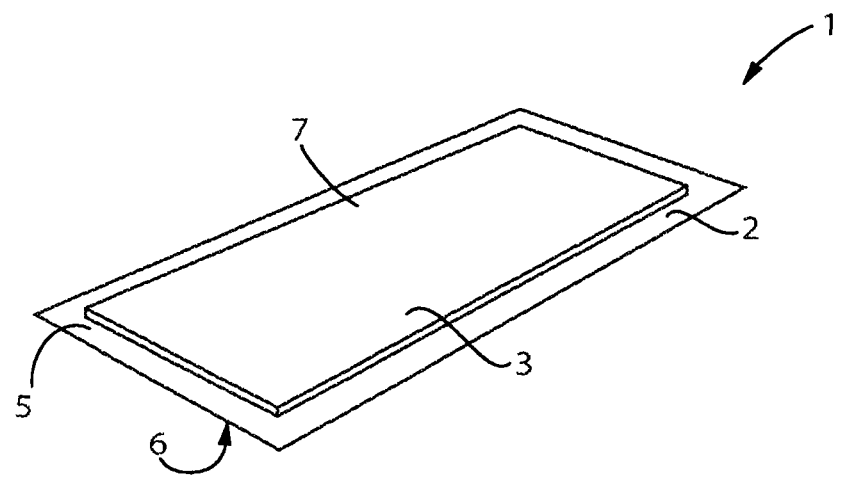
FIG. 1 is a perspective view of a barrier patch, as shown and described herein.

While the specification concludes with the claims particularly pointing out and distinctly claiming the invention, it is believed that the present invention will be better understood from the following description.

All percentages and ratios used herein are by weight of the total composition and all measurements made are at 25° C., unless otherwise designated. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

The term "apply" or "application" as used in reference to a composition, means to apply or spread the compositions of the present invention onto a substrate such as the human skin surface or epidermis.

The term "dermatologically acceptable," as used herein, means that the compositions or components thereof so described are suitable for use in contact with mammalian keratinous tissue without undue toxicity, incompatibility, instability, allergic response, and the like.

The term "facial skin surface" as used herein refers to one or more of forehead, periorbital, cheek, perioral, chin, and nose skin surfaces. While facial skin surfaces are of concern and are exemplified herein, other skin surfaces may be treated with the compositions and methods of the present invention, for example, surfaces typically not covered by clothing such as facial skin surfaces, hand and arm skin surfaces, foot and leg skin surfaces, and neck and chest skin surfaces (for example, décolletage).

The term "keratinous tissue," as used herein, refers to keratin-containing layers disposed as the outermost protective covering of mammals (for example, humans, dogs, cats, etc.) which includes, but is not limited to, skin, mucosa, lips, hair, toenails, fingernails, cuticles, hooves, etc.

The terms "topical application", "topically", and "topical", as used herein, mean to apply (for example, spread, spray) the compositions of the present invention onto the surface of the keratinous tissue.

As used herein, "effective amount" means an amount of a compound or composition sufficient to significantly induce a positive keratinous tissue benefit, including independently or in combination with other benefits disclosed herein. This means that the content and/or concentration of agent in the formulation is sufficient that when the formulation is applied with normal frequency and in a normal amount, the formulation can result in the treatment of one or more undesired keratinous tissue conditions (for example, skin wrinkles). For instance, the amount can be an amount sufficient to inhibit or enhance some biochemical function occurring within the keratinous tissue. This amount of the skin care agent may vary depending upon the type of product, the type of keratinous tissue condition to be addressed, and the like.

The term "safe and effective amount" as used herein means an amount of a compound or composition sufficient to significantly induce a positive benefit, preferably a positive keratinous tissue appearance, including independently or in combinations with the benefits disclosed herein, but low enough to avoid serious side effects, i.e., to provide a reasonable benefit to risk ratio, within the scope of sound judgment of the skilled artisan.

As used herein, "transparent" or "visibly clear" is defined as having the property of transmitting light without appreciable scattering so that bodies lying behind are perceivable. One acceptable test method for determining whether a product is clear or transparent is according to the method provided herein.

The term "translucent", as used herein may include "frosted", "glittered", "pearlescence" and the like and is defined herein as the practice of inducing a low level of light scattering into an otherwise "clear" material causing the material to become matted in appearance.

As used herein, the term "water impermeable" includes materials or objects through which water in its liquid state does not pass.

Barrier Patch

A skin care product or kit is provided herein comprising a cosmetic composition comprising an effective amount of a skin active agent and a barrier patch comprising a backing layer having a first surface and a pressure sensitive adhesive in contact with the first surface; the barrier patch comprising an adhesive release force of from about 50 gms to about 400 gms; a flexibility from about 8 grams to about 40 grams; and a WVTR from about 1 g/m$^2$/24 h to about 500 g/m$^2$/24.

In an embodiment a method of the present invention includes:

a. applying a cosmetic composition to a target area of the skin, comprising an effective amount of a skin active agent;
b. applying a barrier patch to the target area of skin, the barrier patch comprising:
   a backing layer having a first surface;
   a pressure sensitive adhesive in contact with the first surface;
      adjusting the properties of the barrier patch to have;
      an adhesive release force of about 50 gms to about 400 gms; a WVTR of about 1 g/m$^2$/24 h to about 500 g/m$^2$/24 h; and a flexibility of about 8 grams to about 40 grams.

Figure 2:
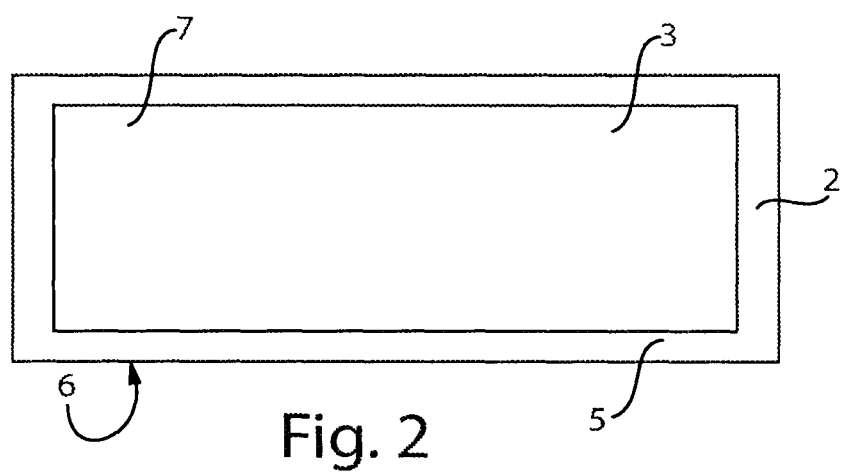
FIG. 2 is a top plan view of the barrier patch of FIG. 1, as shown and described herein.

An exemplary embodiment of the barrier patch 1 is shown in FIGS. 1 and 2. The barrier patch comprises a backing layer 2 and a pressure sensitive adhesive 3. The backing layer has a first surface 5 and a second surface 6. The pressure sensitive adhesive 3 is in contact with at least part of the first surface 5 of the backing layer 2 to form a pressure sensitive adhesive coated region 7 of the first surface 5. In the embodiment of FIGS. 1 and 2, the barrier patch 1 is rectangular, however this shape is not intended to limit the invention.

Figure 3:
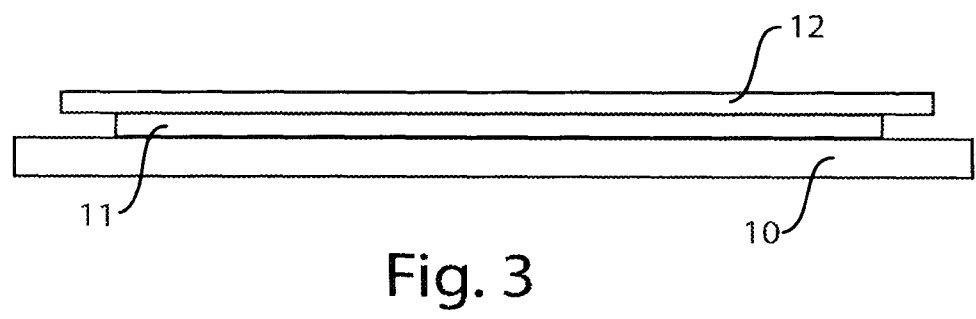
FIG. 3 is a cross section of an alternative barrier patch, as shown and described herein.

A cross section of another exemplary embodiment of a subject barrier patch is shown in FIG. 3 and includes a backing layer 10, a pressure sensitive adhesive 11, and a release layer 12.

The backing layer of the barrier patch of the present invention may comprise a solid sheet material. The sheet provides the primary structure and shape to the patch, allowing it to be handled and applied for treatment of a specific target area of the skin.

The barrier patches have a size and shape adapted to conform to a desired target area of skin which could be a human face or part thereof, legs, hands, arms, feet, or human torso. They may be generally flat in appearance.

The exact size and shape of the barrier patch will depend upon the intended use and product characteristics. The barrier patch herein can be, for example, a square, circle, semicircle, rectangle, triangle, oval, ring, crescent, crescent with rounded corners, teardrop or other more complex and irregular shape. The shape of the barrier patch may be selected from the group consisting of circle, square, rectangle, triangle, and/or irregular shape that conforms to the contours of the forehead, perioral, and/or periorbital areas of the human face.

For a barrier patch shaped to fit the face or other target area of skin, the surface area of the barrier patch may range from about 0.25 $cm^2$ to about 1000 $cm^2$, and/or from about 1 $cm^2$ to about 500 $cm^2$, and/or from about 1 $cm^2$ to about 200 $cm^2$, and/or from about 1 $cm^2$ to about 50 $cm^2$, and/or from about 5 $cm^2$ to about 15 cm Surface area refers to that of a flat plane having the same boundary as the surface i.e. ignoring any surface texturing present.

In an embodiment, the barrier patch typically has an average thickness ranging from about 0.5 mils to about 100 mils, in alternative embodiments the barrier patch has a thickness of about 1 mils to about 35 mils and/or about 2 mils to about 30 mils and/or an average thickness of from about 3 mils to about 15 mils.

In certain embodiments the barrier patch is substantially free of, comprises only non-effective amounts of, or is void of, a skin active agent. As such, the barrier patch of the present invention may be characterized as a "blank" barrier patch. In this regard, in an embodiment an effective amount of the skin active agent employed is a separate component from the barrier patch.

In certain embodiments, the barrier patch comprises a backing layer. According to one embodiment, the barrier patch or backing layer is a film having an WTVR value between about 1 $g/m^2/24$ h to about 500 $g/m^2/24$ h, and in another embodiment has a WVTR from about 1 $g/m^2/24$ h to about 250 $g/m^2/24$ h and/or from about 1 $g/m^2/24$ h to about 180 $g/m^2/24$ h and/or from about 2 $g/m^2/24$ h to about 150 $g/m^2/24$ h and/or from about 2 to about 20 $g/m^2/24$ h. The term WTVR stands for "Water Vapor Transmission Rate" and is measured according to the methods herein.

The backing layer in certain embodiments is non-porous or impermeable to water. Thus in an embodiment the barrier patch or backing layer is water impermeable. In certain other embodiments the backing layer is impermeable to the cosmetic composition, the skin care active agent employed, and fluids wherein the WVTR is from about from about 2 to about 100 $g/m^2/24$ h. While not being bound by theory using a substrate that prevents water loss from the cosmetic composition while the cosmetic composition is in contact with the keratinous tissue and skin, prevents the cosmetic composition from drying out. Water loss from the cosmetic composition may lower the water concentration, may destabilize an emulsion if present, and may increase the concentration of skin active agents. This may result in reduced or loss of efficacy and/or irritation to the skin.

Such relative water impermeability and lower water vapor permeability of the backing layer and barrier patch may increase the effectiveness and efficiency of the cosmetic composition used with the barrier patch. For example, without being bound by theory, the water impermeability and lower water vapor permeability of the backing layer and/or barrier patch employed may serve to enhance or increase the penetration of the skin care active agent into the skin.

In certain embodiments the liquid-impermeable and breathable backing layer and barrier patch may, for example, consist of a perforated polyethylene film, where the size of the holes has been chosen so that air and vapor may pass, but not liquid molecules. Breathable materials can, as mentioned above, consist of perforated plastic films. One example of such film is described in U.S. Pat. No. 5,628,737. The backing layer may also consist of micro-porous plastic films, as is described in, for example, EP-A-0238200.

In one embodiment the barrier patch is polyethylene film sold under the tradename, 1525L, available from 3M, St. Paul, Minn. No. 1525-L has a backing of polyethylene film of approximately 3 mil thickness, a 1.4 mil thick hypoallergenic, pressure sensitive acrylate adhesive layer and a paper release layer coated with polyethylene and silicone.

In certain embodiments, the backing layer is generally Made of a flexible material which is capable of remaining fitted and flexing during the movement of the human body and movements associated with facial expressions or gestures. By "flexible" it is meant that the backing layer may be substantially bent or folded without breaking, tearing, ripping, etc. The barrier patch comprises a flexibility from about 8 grams to about 40 grams and/or about 8 grams to about 25 grams, and/or from about 10 grams to about 25 grams, and/or from about 2 grams to about 10 grams. This degree of flexibility of the barrier patch is selected in combination with the thickness, WVTR, and adhesion release properties, to ensure that desirable conformability and comfort are obtained. The barrier patch also does not collapse or fold under gravity or upon handling and application by the user. It is desirable for the barrier patch to conform to the target area of the skin surface to which it is applied without folding, crinkling, or inducing more wrinkling of the target area of the skin. Accordingly, the barrier patch is readily conformable to the skin and remains flexible throughout the duration of use, as the user moves during the period of time worn. In an embodiment, the flexibility is substantially constant for the entire period of time that the barrier patch is worn by the user.

Since the thickness of the barrier patch will influence flexibility, the substrate thickness should be selected that enables the desired flexibility of the barrier patch to be achieved.

The backing layer of the barrier patch may comprise at least one material, for example, a water impermeable and water vapor permeable material, that includes but is not limited to polypropylene (PP); polyethylene (PE, including HDPE and LLDPE); polyethylene terephthalate (PET); polyvinylchloride (PVC); polyamide (PA); polycarbonate; polyurethane; cellulose acetate; polychloropene; polysulfone; polytetrafluoroethylene (PTFE); polyvinyl acetate (PVA); polyethylene glycol terephthalate film; polystyrene; polyphenylene oxide (PPO); acrylonitrile butadiene styrene (ABS); acrylic; acrylonitrile styrene acrylate (ASA); ethylene vinyl alcohol (EVA); natural rubber, latex, nylon, nitrile, silicone and thermo plastic elastomers (TPE), and combination thereof. The backing layer may comprise a single polymer or mixtures of polymers or copolymers. The barrier patch may comprise a polyolefin, and/or a high density polyethylene. Laminates of these materials may also be used. The materials also may be coextruded. In one embodiment the backing layer or barrier layer is substantially free of a non-woven material.

In one embodiment, to provide for a less visible and less conspicuous barrier patch, the barrier patch is transparent, translucent, and/or visibly clear. One acceptable test method for determining whether a product is clear or transparent is according to the method provided herein which determines the transparency threshold. In one embodiment the barrier patch is transparent and in other embodiment the barrier patch has a transparency threshold from about 1 point to about 10 point, and/or about 1 point to about 4 point, and/or no greater than about 10 point, and/or no greater than about 4 point.

The cosmetic composition and barrier patch, for example, may remain in contact with the target area of skin for a period of time from about 2 hours to about 1 week. Once the period of time has elapsed, the barrier patch is removed by peeling it away from the target area of the skin so that upon removal, the barrier patch is removed intact, i.e., no backing layer material is left on the target area of the skin.

The balance of properties of the barrier patch enables it to be easily and non-traumatically removed from the target area of skin. In certain embodiment the adhesive release force is from about 50 grams to about 400 grams, in another embodiment is from about 75 grams to about 350 grams, and in another embodiment is from about 100 grams to about 200 grams. If the adhesive release force is too low, then the patch does not remain adhered to the target area of skin for the full extended wearing time. If the adhesive release force is too high, the removal of the patch at the end of the wearing period is either painful or is traumatic to the skin. The method of determining the adhesive release force is according to the method herein.

Without being bound by theory, occlusion from the barrier patch serves three important purposes. First, by maintaining a continuously moist environment on the skin, the composition such as an aqueous composition comprising skin active agents can be kept in a liquefied or solubilized form to create a sustained delivery environment compared to traditional gel or lotion carriers alone that become dried on skin. Also, greater hydration/water content in the skin can promote a more favorable thermodynamic/physical environment to enable increased penetration and flux of some actives through layers of the skin, thereby increasing the delivery rate or amount of actives residing in the skin. Finally, building a reservoir of moisture in the skin serves to plump or swell the skin structure.

Figure 8:
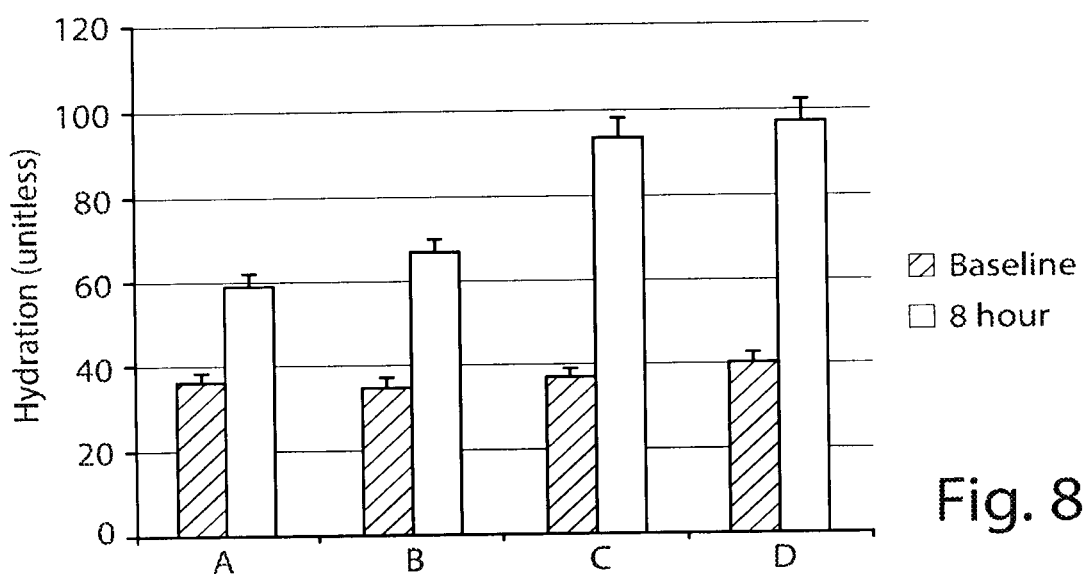
FIG. 8 illustrates the skin hydration effect of four different film materials.

Therefore in one embodiment the method and compositions herein provide for improved hydration of the target area of skin. FIG. 8 illustrates the skin hydration effect of four different film materials. Material A is 2476 from 3M, material B is MEDIPORE H from 3M, material C is 1525L from 3M, and material D is 9830 from 3M. As can be seen in FIG. 8, and according to the Methods provided herein, the hydration of the target area of skin after 8 hours was from about 35 to about 120 and/or from about 38 to about 100 and/or about 40 to about 95 and/or about 45 to about 95.

The barrier patch may be manufactured by any suitable method, including casting, injection moulding, co-injection moulding, over moulding, in-mold assembly, compression moulding, blow moulding, casting thermo or vacuum forming. Where appropriate the barrier patch may be laminated by heat welding (which may further include the use of pressure, ultrasonic forces and radio or high frequencies), co-extrusion; adhesives, electro static adhesions (such as flocking by fibres) and topical surface applications.

A variety of adhesives may be used in the manufacture of the barrier patch herein. Typically, the adhesive material is a pressure-sensitive adhesive (PSA) that is suitable for long-term skin contact, and which should be physically and chemically compatible with the backing layer and/or additives that are present. Examples of suitable adhesive materials include, but are not limited to, the following: acrylic and methacrylic ester homo-or copolymers, butyl rubber based systems, silicones, urethanes, vinyl esters and amides, olefin copolymer materials, natural or synthetic rubbers, hot-melt adhesives (see, for example, U.S. Pat. No. 5,387, 450); polyethylenes; polysiloxanes; polyisobutylenes; polyacrylates; polyaciylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene (polychloroprene) and combinations thereof.

The adhesive typically has an average thickness ranging from about 0.5 mils to about 15 mils, in alternative embodiments about 1 mils to about 5 mils.

In accordance with one embodiment, a method of making a barrier patch is provided comprising:
a. laminating a barrier patch by a process selected from the group consisting of heat welding, ultrasonic force, co-extrusion; adhesion, electro static adhesion and combinations thereof; the barrier patch having a first surface;
b. applying a pressure a pressure sensitive adhesive to the first surface;
the barrier patch having an adhesive release force of about 50 gms to about 400 gms; a WVTR from about 1 g/m$^2$/24 h to about 500 g/m$^2$/24 h; in another embodiment from about 1 g/m$^2$/24 h to about 180 g/m$^2$/24 h and a flexibility from about 8 grams to about 40 grams.

Release Layer

The barrier patch herein may further comprise a protective release layer removably attached to the pressure sensitive adhesive side, for example, first surface, of the backing layer and opposite the second surface of the backing layer. The release layer provides protection for the pressure sensitive adhesive from the environment and prior to application by the user.

The protective release layer may comprise materials including polymer resins such as polyolefins, for example, polypropylene (including stratified biaxially oriented polypropylene (SBOPP)), polyethylene (including LDPE; LLDPE; HDPE; Metallocene) or polyethylene terephthalate, and combinations thereof. Alternative materials which may be used include polyvinylchloride, polyamide, acetyl, acrylonitrile butadiene styrene, acrylic, acrylonitrile styrene acrylate, ethylene vinyl alcohol, ethylene vinyl acetate, Nylon, Latex, natural or synthetic rubbers, polycarbonate, polystyrene, silicone or thermo plastic elastomer, thermo plastic vulcanate or copolymers of said materials, and combinations thereof. In an embodiment the protective release layer may comprise a coating of a non-stick material. Exemplary non-stick coatings include wax, silicone, fluoropolymers such as TEFLON®, and fluorosilicones.

In an embodiment, the protective release layer covers the entire aforementioned area of pressure sensitive adhesive coated region of the backing layer. In another embodiment the protective release layer is water impermeable. In a further embodiment, the release layer has a mean thickness of at least about 85 microns, or from about 85 microns to about 150 microns, and/or from about 90 microns to about 120 microns.

The release layer may optionally extend, in whole or part, beyond the pressure sensitive adhesive coated region of the backing layer and/or beyond the backing layer to provide a removal tab that facilitates ease of removal of the release layer.

Cosmetic Composition
Skin Active Agents

The compositions of the present invention may comprise a skin active agent which provides a particular skin care benefit characteristic of the usage of the skin care product. The skin care benefit may include benefits related to appearance or make-up of the skin. The skin care active can provide acute (immediate and short lived) benefits, or chronic (long term and longer lasting) benefits.

The term "skin active agent" as used herein, means an active ingredient which provides a cosmetic and/or therapeutic effect to the area of application on the skin. The skin active agents useful herein include skin lightening agents, anti-acne agents, emollients, non-steroidal anti-inflammatory agents, topical anaesthetics, artificial tanning agents, anti-microbial and anti-fungal actives, skin soothing agents, sun screening agents, skin barrier repair agents, anti-wrinkle agents, anti-skin atrophy actives, lipids, sebum inhibitors, sebum inhibitors, skin sensates, protease inhibitors, anti-itch agents, desquamation enzyme enhancers, anti-glycation agents, and mixtures thereof. When included, the present composition comprises a safe and effective amount of a skin active agent and/or from about 0.001% to about 20%, in another embodiment from about 0.1% to about 10% of at least one skin active agent.

The type and amount of skin active agents are selected so that the inclusion of a specific agent does not affect the stability of the composition. For example, hydrophilic agents may be incorporated in an amount soluble in the aqueous phase, while lipophilic agents may be incorporated in an amount soluble in the oil phase.

Other skin active agents purported to exhibit expression-line relaxing benefits for use in the present invention include, but are not limited to, Lavandox available from Barnet Products Corporation; Thallasine 2, available from BiotechMarine; Argireline NP, available from Lipotec; Gatuline In-Tense and Gatuline Expression, available from Gattefosse; Myoxinol LS 9736 from BASF Chemical Company, Syn-ake, available from DSM Nutritional Products, Inc.; and Instensyl®, available from Silab, Inc; Sesaflash™, available from Seppic Inc.

Skin lightening agents useful herein refer to active ingredients that improve hyperpigmentation as compared to pretreatment. Useful skin lightening agents herein include ascorbic acid compounds, vitamin $B_3$ compounds, azelaic acid, butyl hydroxyanisole, gallic acid and its derivatives, glycyrrhizinic acid, hydroquinone, kojic acid, arbutin, mulberry extract, and mixtures thereof. Use of combinations of skin lightening agents is believed to be advantageous in that they may provide skin lightening benefit through different mechanisms.

Ascorbic acid compounds useful herein include ascorbic acid per se in the L-form, ascorbic acid salt, and derivatives thereof. Ascorbic acid salts useful herein include, sodium, potassium, lithium, calcium, magnesium, barium, ammonium and protamine salts. Ascorbic acid derivatives useful herein include, for example, esters of ascorbic acid, and ester salts of ascorbic acid. Particularly preferred ascorbic acid compounds include 2-o-D-glucopyranosyl-L-ascorbic acid, which is an ester of ascorbic acid and glucose and usually referred to as L-ascorbic acid 2-glucoside or ascorbyl glucoside, and its metal salts, and L-ascorbic acid phosphate ester salts such as sodium ascorbyl phosphate, potassium ascorbyl phosphate, magnesium ascorbyl phosphate, and calcium ascorbyl phosphate. Commercially available ascorbic compounds include magnesium ascorbyl phosphate available from Showa Denko, 2-o-D-glucopyranosyl-L-ascorbic acid available from Hayashibara and sodium L-ascorbyl phosphate with tradename STAY C available from Roche.

Vitamin $B_3$ compounds useful herein include, for example, those having the formula:

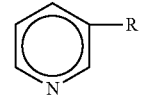

wherein R is —$CONH_2$ (for example, niacinamide) or —$CH_2O_H$ (for example, nicotinyl alcohol); derivatives thereof; and salts thereof. Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide. Preferred vitamin $B_3$ compounds are niacinamide and tocopherol nicotinate, and in another embodiment is niacinamide. In a preferred embodiment, the vitamin $B_3$ compound contains a limited amount of the salt form and is more preferably substantially free of salts of a vitamin $B_3$ compound. Preferably the vitamin $B_3$ compound contains less than about 50% of such salt, and is more preferably essentially free of the salt form. Commercially available vitamin $B_3$ compounds that are highly useful herein include niacinamide USP available from Reilly.

Other hydrophobic skin lightening agents useful herein include ascorbic acid derivatives such as ascorbyl tetraisopalmitate (for example, VC-IP available from Nikko Chemical), ascorbyl palmitate (for example, available from Roche Vitamins), ascorbyl dipalmitate (for example, NIKKOL CP available from Nikko Chemical); undecylenoyl phenyl alanine (for example, SEPIWHITE MSH available from Seppic); octadecenedioic acid (for example, ARLATONE DIOIC DCA available from Uniquema); *Oenothera biennis* seed extract, and *Pyrus malus* (apple) fruit extract, Water and Myritol 318 and butylene glycol and tocopherol and sscorbil tetraisopalmitate and Paraben and Carbopol 980 and DNA/SMARTVECTOR UV available from COLETICA, magnesium ascorbyl phosphate in hyaluronic filling sphere available from COLETICA, and mixtures thereof.

Other skin active agents useful herein include those selected from the group consisting of N-acetyl D-glucosamine, panthenol (for example, DL panthenol available from Alps Pharmaceutical Inc.), tocopheryl nicotinate, benzoyl peroxide, 3-hydroxy benzoic acid, flavonoids (for example, flavanone, chalcone), farnesol, phytantriol, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, retinyl esters (for example, retinyl propionate), phytic acid, N-acetyl-L-cysteine, lipoic acid, tocopherol and its esters (for example, tocopheryl acetate: DL-$\alpha$-tocopheryl acetate available from Eisai), azelaic acid, arachidonic acid, tetracycline, ibuprofen, naproxen, ketoprofen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neomycin sulfate, theophylline, and mixtures thereof.

The compositions of the present invention in various embodiments may comprise N-acyl amino acid compounds. Suitable N-acyl amino acid compounds include, but are not limited to, N-acyl phenylalanine, N-acyl tyrosine, their isomers, including their D and L isomers, salts, derivatives, and mixtures thereof. An example of a suitable N-acyl amino acid is N-undecylenoyl-L-phenylalanine and is commercially available under the tradename SEPIWHITE (Registered trademark) from Seppic (France).

Skin care agents are also disclosed in US Publication No. 2007/0020220A1, published Jan. 25, 2007, wherein the components/ingredients are incorporated herein by reference in their entirety.

The cosmetic composition may comprise one or more peptides. Herein, "peptide" refers to peptides containing ten or fewer amino acids, their derivatives, isomers, and complexes with other species such as metal ions (for example, copper, zinc, manganese, and magnesium). As used herein, peptide also refers to both naturally occurring and synthesized peptides. In one embodiment, the peptides are di-, tri-, tetra-, penta-, and hexa-peptides, their salts, isomers, derivatives, and mixtures thereof. Examples of useful peptide derivatives include, but are not limited to, peptides derived from soy proteins, palmitoyl-lysine-threonine (pal-KT) and palmitoyl-lysine-threonine-threonine-lysine-serine (pal-KTTKS, available in a composition known as MATRIXYL®) palmitoyl-glycine-glutamine-proline-arginine (pal-GQPR, available in a composition known as RIGIN®), these three being available from Sederma, France, and Cu-histidine-glycine-glycine (Cu-HGG, also known as IAMIN®). In various embodiments the cosmetic composition may comprise from about $1 \times 10^{-7}$% to about 20% alternatively from about $1 \times 10^{-6}$% to about 10%, and alternatively from about $1 \times 10^{-5}$% to about 5% of the peptide.

In one embodiment, the skin active agent is niacinamide. In one embodiment, the agent is a combination of niacinamide, glycerine, tocopherol acetate, and D-panthenol. Niacinamide may be included in the composition in an amount between about 1% to about 30 wt %, in another embodiment from about 2% to about 28 wt %, in another embodiment from about 5% to about 25 wt %, and in another embodiment from about 10% to about 20 wt %. When D-panthenol is included, it may be present in an amount of about 0.5% to about 5 wt %, or about 0.5% to about 3 wt % and/or about 0.5% to about 2 wt %. Glycerin may be included as an active in an amount from about 6% to about 20 wt %, and/or from about 8% to about 15 wt %, and/or from about 10% to about 15 wt %.

In various embodiments, the skin active agent is selected from niacinamide, alone or in combination with one or more of palmitoyl-lysine-threonine, palmitoyl-lysine-threonine-threonine-lysine-serine, N-undecyl-10-enoyl-L-phenylalanine, retinyl propionate, N-acetyl glucosamine, vitamin C, tretinoin, salicylic acid, benzoic acid, benzoyl peroxide, tretinoin, and combinations thereof.

In an embodiment the cosmetic compositions herein may be aqueous solutions, or emulsions such as oil-in-water emulsions, water-in-oil emulsions or multiple emulsions having aqueous or oily external phases. In another embodiment the cosmetic compositions herein are oil-in-water emulsions.

In one embodiment to avoid a negative interaction with the pressure sensitive adhesive, the cosmetic composition comprises only low levels of silicones of about 0.5% to about 10%, and/or from about 1% to about 5% and/or the cosmetic composition is substantially free of silicones. As used herein "silicones" may refer to those silicones disclosed in US 2007/0020220A1, published Jan. 25, 2007, Osborne, for example, in paragraphs [0226] to [0258].

In one embodiment the cosmetic composition is substantially free of depilatory agents.

The cosmetic composition may comprise an effective amount of a skin active agent having activity to improve visual or aesthetic appearance of the skin, such as an agent effective to reduce or diminish the appearance of fine lines and/or wrinkles on human facial skin or an agent effective to treating existing acne lesions, reducing redness associated with acne lesions and/or protecting from formation of acne lesions.

The methods of treatment, application, regulation, or improvement disclosed herein may utilize the aforementioned compositions. Application of the present compositions can occur on any target area of skin surface of the body. Skin surfaces of the most concern tend to be those not typically covered by clothing such as facial skin surfaces, hand and arm skin surfaces, foot and leg skin surfaces, and neck and chest skin surfaces (for example, décolletage). In particular, application may be on a facial skin surface including the forehead, perioral, chin, periorbital, nose, and/or cheek skin surfaces.

The step of applying the cosmetic composition to a target area of skin may be done by localized application to the target area, for example, an area that contains wrinkles. In reference to application of the composition, the term "localized", "local", or "locally" mean that the composition is delivered to the target area of skin (such as an area of skin containing wrinkles) while minimizing delivery to skin surface not requiring treatment. The composition may be applied and lightly massaged into the skin. It is recognized that localized application does allow for a reasonable amount of the composition to be applied to areas adjacent to the wrinkles to be treated (i.e., the composition is unlikely to be applied or to remain within the boundary of the wrinkles without some spreading). The form of the composition or the dermatologically acceptable carrier should be selected to facilitate-localized application. While certain embodiments of the present invention contemplate applying a composition locally to a wrinkled area, it will be appreciated that compositions of the present invention can be applied more generally or broadly to one or more facial skin surfaces to reduce the appearance of wrinkles within those facial skin regions.

The method of treating skin herein may optionally begin with a cleansing step. The consumer can wash his or her face with a suitable cleanser (for example, Olay Purifying Mud Lathering Cleanser, available from The Procter & Gamble Company, Cincinnati, Ohio), and gently dry his or her skin with a towel.

While some methods described herein contemplate applying the compositions of the present invention with an applicator, it will be appreciated that applicators are not required and the cosmetic compositions of the present invention can also be applied directly by using one's finger or in other conventional manners.

Kits

Also provided herein are kits, where the kits at least include one or more barrier patches and a cosmetic composition comprising an effective amount of a skin active agent, as described herein.

Thus in an embodiment a skin care kit is provided comprising:
a cosmetic composition comprising an effective amount of a skin active agent:
one or more barrier patches comprising a backing layer having a first surface; a pressure sensitive adhesive in contact with the first surface; an adhesive release force of from about 50 gms to about 400 gms; a flexibility from about 8 grams to about 40 grams; and a WVTR from about 1 $g/m^2/24$ h to about 500 $g/m^2/24$ h. The kit may comprise a display package comprising a display surface or an inclined display surface, defining a first cavity to contain a cosmetic composition and a second cavity to contain a plurality of barrier patches.

Figure 4:
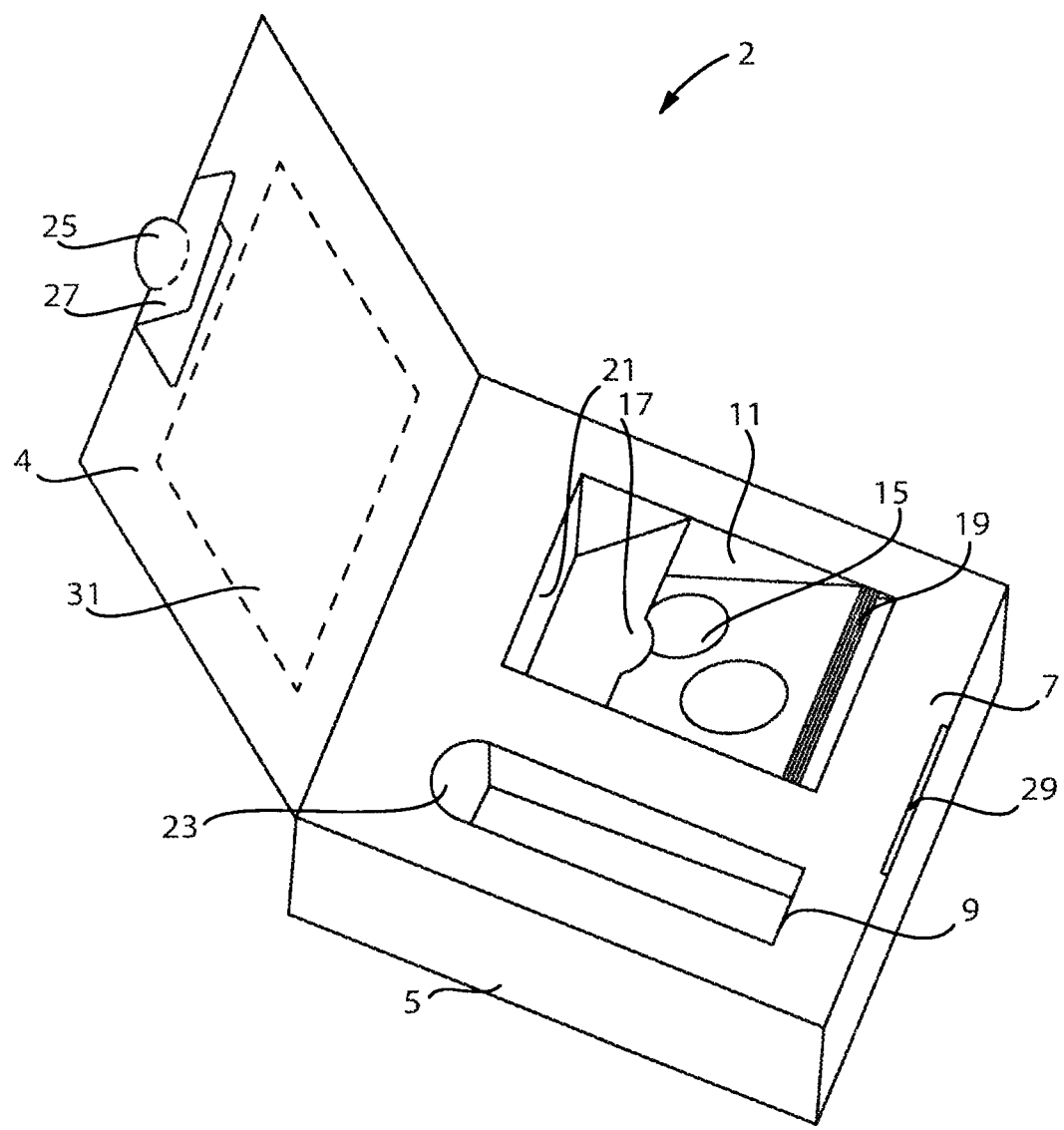
FIG. 4 is a perspective side view of an embodiment of the display package.

As shown in FIG. 4 a display package 2 is provided, comprising a display surface 7 or an inclined display surface (shown in FIGS. 5 and 6), defining a first cavity 9 to contain the cosmetic composition and a second cavity 11 to contain a plurality of barrier patches 15.

The display package 2 may comprise a top lid 4; a bottom support tray 5 having a display surface 7, defining a first cavity 9 to contain a cosmetic composition (not shown) and a second cavity 11 to contain a plurality of barrier patches 15; wherein the cosmetic composition may be positioned substantially within the first cavity 9.

In another embodiment the second cavity 11 further comprises one or more retention tabs 17. As shown in FIG. 4 the retention tab 17 may be positioned closer to the surface of the sheets in unit dose form 19 or the retention tab 17 may be placed in a vertical position against the backwall 21 of the second cavity 11 to make removal of the one or more sheets in unit dose form 19 easier to remove from the second cavity 11.

In an embodiment the display package 2 contains a plurality of sheets in unit dose form 19 wherein each sheet comprises no more than 2 barrier patches 15, as shown in FIG. 4. Moreover, the first cavity 9 may comprise a substantially identical dimension and/or a substantially identical geometric shape of the container for the cosmetic composition.

In further embodiments shown in FIG. 4 the display package 2 may have a first cavity 9 comprising a removal aid 23 to assist in the removal of the cosmetic composition from the first cavity 9. The removal aid 23 may comprise a gap in one end of the first cavity 9 to provide an open area so that a user may be able to insert his or her fingertip into the gap in order to remove a cosmetic composition that is positioned substantially within the first cavity, from the first cavity 9.

The display package 2 may also comprise an opening tab 25 to aid in opening or closing the display package 2. The top lid 4 may further comprise a opening flap 27 that is configured to be seated into the closure slot 29 when the top lid is closed. Use instructions 31 may also be present on the inside surface of the top lid 4.

Figure 5:
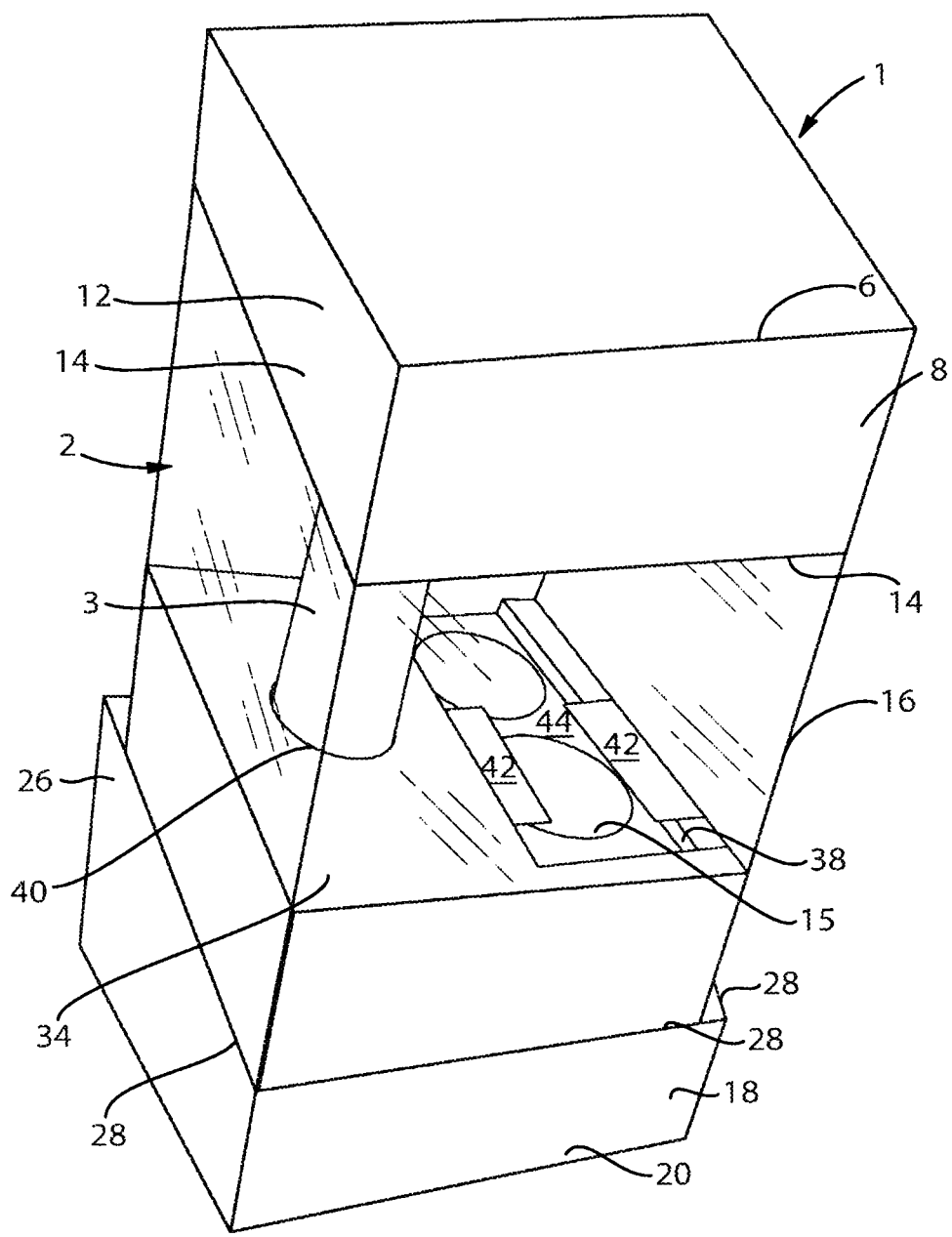
FIG. 5 is a perspective side view of another embodiment of a display package.

FIG. 5 shows another embodiment of the skin care kit 1 comprising: a cosmetic composition 3 comprising an effective amount of a skin active agent. The skin care kit further comprises a barrier patch 15 comprising a backing layer having a first surface and a pressure sensitive adhesive in contact with the first surface; a WVTR from about 1 $g/m^2/24$ h to about 500 $g/m^2/24$ h; the barrier patch optionally further comprising an adhesive release force of from about 50 gms to about 400 gms and optionally further comprises a flexibility from about 8 grams to about 40 grams.

Figure 6:
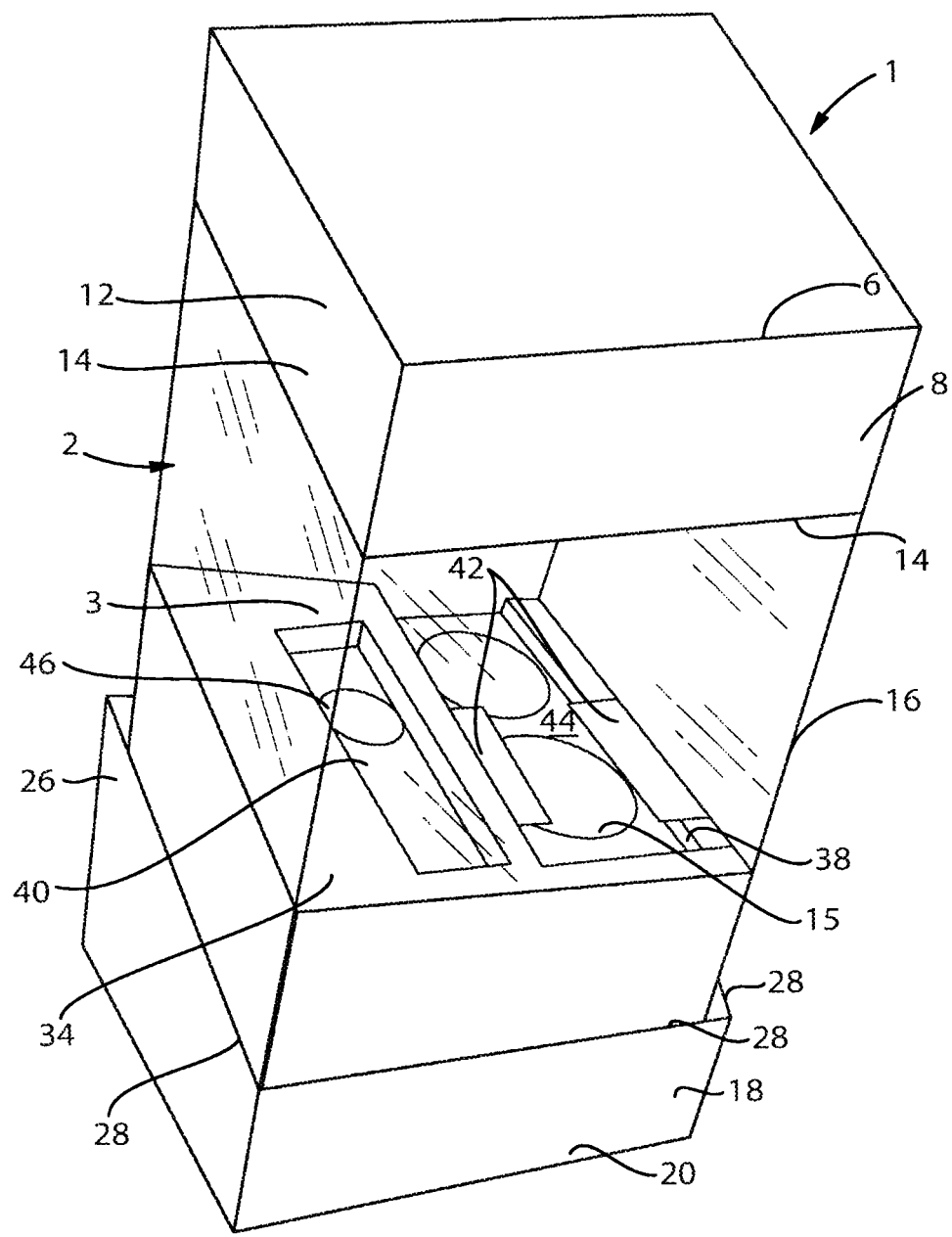
FIG. 6 is a perspective side view of another embodiment of a display package.

The display package 2 of FIGS. 5 and 6 may comprise a top cover 6 having a front wall 8, a back wall 10 (not shown) and two sidewalls 12: the top cover 6 further comprising edges 14 of the front wall 8, a back wall 10 and two sidewalls 12. The display package 2 of FIGS. 5 and 6 may also comprise a base 18 having a front wall 20, a back wall 22 (not shown) and two sidewalls 26; an intermediate surround window 16 that may be at least partially transparent; an inclined display surface 34, wherein the intermediate surround window 16 and the inclined display surface 34 are positioned between said top cover 6 and said base 18. The inclined display surface 34 may define a first cavity 40 to contain a cosmetic composition 3 and a second cavity 38 to contain a plurality of barrier patches 15.

As shown in FIGS. 5 and 6, in an embodiment the barrier patches 15 are provided in one or more sheet unit dose forms 44 wherein, for example, the sheet unit dose forms 44 comprise no more than 2 barrier patches 15. The second cavity 38 may also comprise one or more retention tabs 42 that prevent or minimize the sheet unit dose forms from sliding out of the second cavity 38.

In an embodiment the cosmetic composition (or container holding the cosmetic composition) 3 may either be positioned substantially within the first cavity 40 wherein the first cavity is configured to house the cosmetic container, or the first cavity 40 may be configured to house the cosmetic composition 3 in an upright position in the first cavity 40. In an embodiment in FIG. 6 the first cavity 40 may further comprise a receptacle 46 which may enable the cosmetic composition (or container) to be positioned in an upright position relative to the display surface or the inclined display surface 34. Moreover, in the same first cavity the cosmetic composition may also be stored in a position substantially parallel to the display surface or inclined display surface.

The skin care kit 1 may further comprise edges 14 of the front wall 8, back wall 10 and two sidewalls 12 of the top cover 6 that are configured to mate with the edges 28 of the front wall 20, back wall 22 and two sidewalls 26 of the base 18 when the intermediate surround window 16 is removed, to provide a close fitting relationship between the edges 14 of the top cover 6 and the edges 28 of the base 18.

In another embodiment the second cavity 38 further comprises one or more retention tabs 42 to maintain the sheet unit dose forms 44 of the barrier patches 15 in place so that the sheet unit dose forms of the barrier patches do not side relative to the inclined display surface 34.

Figure 7:
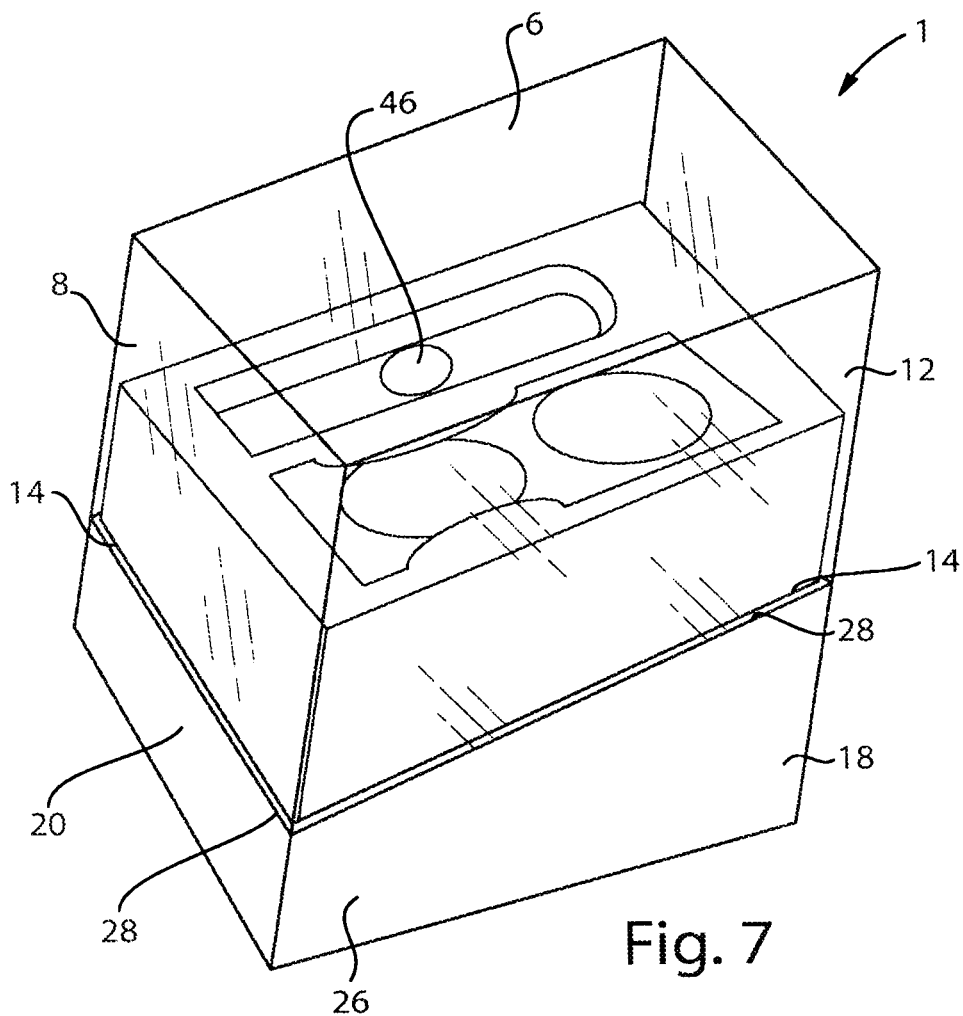
FIG. 7 is a perspective side view of another embodiment of a display package.

As shown in FIG. 7, in an embodiment the skin care kit 1 may comprise edges 14 of the front wall 8, back wall 10 and two sidewalls 12 of the top cover 6 that are configured to mate with the edges 28 of the front wall 20, back wall 22 and two sidewalls 26 of the base 18 when the intermediate surround window 16 is removed, to provide a close fitting relationship between the edges 14 of the top cover 6 and the edges 28 of the base 18. The top cover 6 may be transparent or opaque.

In an embodiment the first cavity 40 comprises a substantially identical dimension and/or geometric shape of the cosmetic composition (or container) 3.

As used herein "a sheet unit dose form" means one or a plurality of sheets (for example, continuous film sheets), that may have, for example, from about 1 to about 6, barrier patches. Moreover, the sheet unit dose form may serve as the release layer for the barrier patch.

In an embodiment one or more barrier patches may be sealed in an individual package so that one barrier patch or a relatively smaller number may be removed from the packaging and used while the packaging of any other barrier patches of the kit remain intact or un-breached.

As mentioned above, the kits may also include a cosmetic composition, for example, an aqueous cosmetic composition, comprising an effective amount of a skin active agent. The dosage amount of formulation provided in a kit may be sufficient for a single application or for multiple applications. Accordingly, in certain embodiments of the subject kits a single dosage amount of the skin active agent is present in a kit. For example, a kit may include a single barrier patch and a single dosage amount of the cosmetic composition.

In certain other embodiments, multiple dosage amounts of the cosmetic composition may be present in a kit. For example, a kit may include a plurality of barrier patches and multiple dosage amounts of the cosmetic composition. In those embodiments having multiple dosage amounts of the cosmetic composition, such may be packaged in a single container, for example, a single tube, bottle, vial, and the like (as shown in FIG. 5), or one or more dosage amounts may be individually packaged such that certain kits may have more than one container of a cosmetic composition. In this instance the inclined display surface 34 or the display surface 7 may have one or more first cavities to contain each of the cosmetic compositions or to contain multiple cosmetic compositions. In one embodiment the number of dosage amounts of the cosmetic composition and the number of barrier patches are the same.

In certain other embodiments, the kit comprises multiple barrier patches that are of a size and shape to treat different areas of the face such as for the treatment of age spots, the forehead, the under eye area and the under eye area combined with the crows feet area around the eye.

The subject kits also generally include instructions for how to use the barrier patch to occlude the cosmetic composition in order to deliver the skin active agent to a target area of the skin. In one embodiment the kit includes instructions to provide an effective amount of a skin active agent to the target area of skin that will provide a layer of the cosmetic composition having a thickness from about 10 microns to about 30 microns and/or from about 12 microns to about 25 microns. In another embodiment the kit includes instructions to provide from about 0.5 mg/cm2 to about 3 mg/cm2 of the cosmetic composition, and/or from about 1 ng/cm2 to about 2 mg/cm2 to the target area of skin. In one embodiment and without being bound by theory, the use of the proper amount of the cosmetic composition will minimize the interaction of the cosmetic composition with the pressure sensitive adhesive.

Test Methods

WVTR

WVTR of the barrier patch is measured according to ASTM F1249 at 37° C. and 35% RH. Samples may be analyzed on a MOCON Permatran-W 3/33 Water Vapor Permeability Instrument using ASTM F1249. For samples with higher WVTR (for example, from approximately 300 $g/m^2/24$ h to 500 $g/m^2/24$ h) samples may be analyzed per ASTM E-96 with desiccant placed inside the test cups and 35% RH surrounding the exterior of the cups. Samples of barrier patches are prepared and include the pressure sensitive adhesive.

Adhesive Release Force

Adhesion measurements were evaluated with a ChemInstruments AR1000. Specimens are cut to segments 2 cm wide. One end of a 5 cm-long specimen is placed on a stainless steel test panel and rolled with a 4.5-lb hand-roller. The specimen then stays in contact with the plate for a period of 4 hours. The panel is placed into the instrument at 37-C and the other end of the specimen is attached to the grip set at a 180° peel using Nexcare® gentle paper tape (¾" wide) as a coupler. The speed is set to 10 in/minute and the measurement is initiated. After data collection the initial (onset of pull) and final (pull-off) regions are discarded and the central region where there is constant pull against the specimen is used to generate an average peel force. Peel forces from three specimens are averaged to generate a peel force for each sample.

Transparency

Transparency is measured by assessing the visibility of printed text through the barrier patch. The printed text is prepared by printing the English alphabet (capital letters) onto transparency film (Universal Office Supplies) using Microsoft Word Arial font and a LaserJet 4 Plus printer (Hewlett Packard) fitted with a black ink cartridge. Printed transparency films are prepared in font sizes ranging from 4 points to 28 points. The printed transparency films are then laid over white paper sheets to ensure a uniform background and all samples assessed under normal indoor lighting conditions, such as retail outlet lighting conditions.

The word and/or letters must be visible and/or readable by an individual using unaided 20/20 eyesight and positioned 12 inches in front of the sample.

A sample of the barrier patch, including the backing layer and the pressure sensitive adhesive, of interest is selected. This sample is placed, pressure sensitive adhesive side facing uppermost, onto the transparency film printed with 4 font size. The visibility of the printed text is assessed through the sample. If the text is not legible through the sample, the sample is transferred to the next largest font size print and the assessment repeated. This process is repeated until a font size is reached that is legible through the sample.

The smallest font size legible through the sample is then assigned the "transparency threshold" for that device.

In one embodiment the "transparency threshold" for the sample of the barrier patch of the present invention is no greater than about 10 point, in another embodiment no greater than about 7 point and in yet another embodiment is no greater than about 4 point.

Corneometer Testing

Improvements in skin hydration may be measured with a corneometer, while baseline measurements are taken prior to application of materials. In particular, skin hydration based upon measurements of capacitance may be assessed using the Corneometer (Registered trademark) 825. Use of a Corneometer is further described in U.S. patent application Ser. No. 13/007,630. Such measurements can be non-invasive and can be taken in duplicate on the target area of skin at the following times: At baseline, and 8 hours post-treatment.

Data can be recorded electronically using direct data entry and data capture programs. Measurements can be performed according to a test facility's standard operating procedures and/or the Instrument Operation Manual.

The Corneometer values are arbitrary units for electrical impedance. At baseline, for subjects having a dry skin grade from about 2.5 to about 4.0, an adjusted mean of such Corneometer values can typically fall within a range of about 15 to about 20. Higher Corneometer values can correspond to a higher hydration level, and thus, lower Corneometer values can correspond to lower hydration levels. The same instrument(s) and operator(s) can be used throughout the study.

The probe can be wiped with a Kimwipe between each measurement. At the end of an evaluation session, data collected for that period can be backed up according to instructions in the Instrument Operation Manual, and a hard copy of the data can be printed.

Flexibility

Rigidity or flexibility is measured using a Handle-O-Meter, model #211, available from Thwing-Albert Instrument Co. of Philadelphia, Pa. A 100-g beam was used. For the sample, a specimen was cut to a square of 50 mm width and length. The specimens should be cut in each of the principle directions of the sample, avoiding creases and wrinkles. The samples are tested in four positions (one in each direction and one on each side of the sample), with an average rigidity reported for the 4 positions. For samples with adhesive material, a 1 mil polyethylene film was attached to the sample to cover the adhesive. To account for the effect on flexibility of the 1 mil polyethylene film used as a cover, the flexibility of the 1 mil film was tested separately. This flexibility value was then subtracted from the flexibility value of the sample without the cover film. For thicker samples, it may be necessary to cut samples with dimensions smaller that 50 mm×50 mm to allow the Handle-O-Meter to be able to depress the samples into the slot.

EXAMPLES

The following are non-limiting examples of compositions of the present invention. The examples are given solely for the purpose of illustration and are not to be construed as limitations of the present invention, as many variations thereof are possible without departing from the spirit and scope of the invention, which would be recognized by one of ordinary skill in the art.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the present invention as described herein.

Examples 1-5: Cosmetic Compositions

| Example | 1 | 2 | 3 |
|---|---|---|---|
| Phase A | | | |
| Distilled water | qs 100 | qs 100 | qs 100 |
| Phase B | | | |
| Glycerin | 5 | 5 | 5 |
| TiO2 | 0.75 | 0.75 | 0.75 |
| Phase C | | | |
| glycerin | 1 | 1 | 1 |
| EDTA | 0.1 | 0.1 | 0.1 |
| Carbopol 954 | 0.68 | 0.5 | 0.5 |
| Carbopol 1382 | 0.1 | 0.1 | 0.1 |
| Phase D | | | |
| Cetyl Alcohol | 0.72 | 0.72 | 0.72 |
| Stearyl Alcohol | 0.48 | 0.48 | 0.48 |
| Stearic Acid | 0.1 | 0.1 | 0.1 |
| PEG-100 Stearate | 0.1 | 0.1 | 0.1 |
| Arlatone 2121 | 1 | 1 | 1 |
| Silicone Q21403 | 2 | 2 | 2 |
| Fatty acid ester of sugar | 0.67 | 0.67 | 0.67 |
| Tocopherol Acetate | 0 | 0 | 0.5 |
| Niacinamide | 2 | 2 | 2 |
| Phase E | | | |
| distilled water | 2 | 2 | 2 |
| NaOH to neutralize Carbopols | to neutralize | to neutralize | to neutralize |
| Phase F | | | |
| Urea | 2 | 0 | 0 |
| D-Panthenol | 0 | 0 | 0.5 |
| distilled water | 5 | 5 | 5 |
| Phase G | | | |
| Glydant Plus | 0.1 | 0.1 | 0.1 |
| Glycerin | 1 | 1 | 1 |
| distilled water | 1 | 1 | 1 |
| Phase H | | | |
| Methyl Isostearate | 1.33 | 0 | 0 |
| Isopropyl Isostearate | 0 | 1.33 | 1.33 |
| Retinol | 0 | 0 | 0.04 |
| BHT | 0 | 0 | 0.05 |
| Tween 20 | 0 | 0 | 0.04 |

| Example | 4 | 5 |
|---|---|---|
| Phase A | | |
| distilled water | qs 100 | qs 100 |
| Phase B | | |
| Glycerin | 6 | 6 |
| TiO2 | 0.75 | 0.75 |
| Phase C | | |
| Glycerin | 3 | 3 |
| Carbopol 954 | 0.4 | 0.4 |
| EDTA | 0.1 | 0.1 |
| Phase D | | |
| Cetyl Palmitate | 1.5 | 1.5 |
| Cetyl Alcohol | 2.25 | 2.25 |
| Stearyl Alcohol | 1.5 | 1.5 |
| Stearic Acid | 0.31 | 0.31 |
| PEG-100 Stearate | 0.31 | 0.31 |
| Silicone Wax DC2501 | 2 | 2 |
| DC 3225C | 1.88 | 1.88 |
| Dimethicone 200/350 cst | 0.63 | 0.63 |
| Tocopherol Acetate | 0 | 0.5 |
| Niacinamide | 2 | 2 |
| Phase E | | |
| distilled water | 2 | 2 |
| NaOH to neutralize Carbopol | to neutralize | to neutralize |
| Phase F | | |
| D-Panthenol | 0 | 0.5 |
| distilled water | 0 | 5 |
| Phase G | | |
| Glydant Plus | 0.1 | 0.1 |
| distilled water | 1 | 1 |
| glycerin | 1 | 1 |

-continued

Phase H

| Isopropyl Palmitate | 1.25 | 1.25 |
| Retinol | 0 | 0.04 |
| Tween 80 | 0 | 0.04 |
| BHT | 0 | 0.05 |

Oil-in-water emulsions are prepared from the ingredients in these examples using conventional formulating techniques. First, sparge Phase A ingredients using nitrogen for approximately 15 minutes. Phase B ingredients are milled until the Ti02 is homogeneously dispersed, and then added to Phase A. Phase C ingredients are then dispersed into Phase A/B until uniform using propeller type mixing and heating the mixture to about 75° C. In a separate vessel, Phase D ingredients are combined and heated to about 75' C. The mixture of phases A/B/C are then blanketed with a slow, steady stream of nitrogen. Next the Phase D ingredients are homogenized into the mixture of phases A/B/C using any rotor/stator type of homogenizer for approximately 15 minutes. After the 15 minutes, the mixing is switched to low rpm sweep mixing. Next, phase E ingredients are combined and added to the mixture of phases A-D.

Once phase E is mixed and the batch mixture is homogeneous, the entire batch mixture is cooled. When the batch is cooled to about 50° C., phase F ingredients are added and homogenized. When the batch is cooled to about 40° C., phase G ingredients are added to the batch mixture. Lastly, when the batch mixture is cooled to about 30° C., the phase H ingredients are combined to the batch mixture. Mixing is continued until the batch mixture is uniform.

Delivery of Skin Active Agent to a Target Area of Skin.

The above compositions 1, 2, 3, 4 and/or 5 are applied via the fingertips to the periorbital area of the face of a human test subject to provide from about 0.5 mg/cm2 to about 3 mg/cm2 of the cosmetic composition to the target area of skin. Thereafter an exemplary orbital barrier patch for treatment of periorbital skin aging is attached to periorbital area, hovering the cosmetic composition. The barrier patch is transparent and comprises an adhesive release force of about 150 grams, a WVTR of about 3 g/m$^2$/24 h, and a flexibility of about 10 grams. The barrier patch of the invention is applied and worn for an extended period of time of approximately 7-8 hours and thereafter removed. The method herein delivers an effective amount of the skin active agent in a manner that achieves penetration of the skin active agent into the stratum corneum, and/or other layers of the epidermis, and in many embodiments, into the basal skin layer and/or dermis.

Example 6

A consumer, small-base paired comparison of a patch prototype, 3M 1525L (C), against a series of other commercial patch materials was conducted. The commercial patch materials varied in WVTR, flexibility and adhesive release force values as indicated below in Table 2. The materials included 9776, 9904, 9916, 2476P and 2475P, available from 3M.

Each consumer applied a cosmetic composition. Olay Anti Wrinkle Results Eye Cream, via the fingertips to the periorbital area of their face delivering approximately from 0.5 mg/cm$^2$ to 3 mg/cm$^2$ of the cosmetic composition to the target area of skin. After applying the cosmetic composition, the test subjects applied one of the barrier patches listed below and adhered it to the periorbital area, covering or overlapping the cosmetic composition. The barrier patch was worn for approximately 7-9 hours, generally overnight while sleeping, and thereafter removed. This regimen was repeated for each of five consecutive days. Then consumers answered a questionnaire about the comfort, ease of use and performance of the product.

TABLE 2

| Patch | 1525L (Sample C) | 9776 (Sample U) | 9904 (Sample X) | 9916 (Sample R) | 2476P (Sample S) | 2475P (Sample T) |
| --- | --- | --- | --- | --- | --- | --- |
| Thickness (mil) | 4.4 | 34 | 11 | 15 | 14.6 | 4.6 |
| Backing Layer | Polyethylene | Polyethylene | Polyurethane | Spunlace nonwoven | Spunlace polyester | Thermoplastic elastomer |
| Adhesive | Acrylate | Acrylate | Acrylate | Acrylate | Silicone | Silicone |
| Handle-O-Meter (g) | 14.2 | 106.5 | 24.9 | 40.4 | 13.4 | 5.5 |
| Peak Adhesion (g) | 352.4 | 387.5 | 784 | 2441 | 108 | 77.3 |
| WVTR (g/m2-day) | 2.6 | 15 | 79 | 813 | 225 | 198 |
| Overall Rating[1] | Sample C-51 | Sample C-36 Sample U-48 | Sample C-50 Sample X-41 | Sample C-52 Sample R-42 | Sample C-55 Sample S-52 | Sample C-60 Sample T-35 |

[1]For the overall ratings, each Sample was rated and compared to Sample C.

Consumers prefer, via the overall rating score, 1525L having an adhesive force of 352.4 g, a flexibility of 14.2, and a WVTR of 2.6, to all of the other patches with the exception of 9776. However, 9776 had significantly higher stiffness than 1525L having a flexibility of 106.5 and consumers rated 9776 less comfortable to wear. 2475P, the most flexible patch, had the lowest score. It was difficult to handle and apply by consumers.

For the overall ratings, each Sample was rated and compared to Sample C.

Thus providing barrier patches with the right balance of adhesion, flexibility, and WVTR properties provides preferred product attributes. Water Vapor Transmission Rate provides a degree of occlusion and skin hydration; proper flexibility allows the barrier patch to conform to face and not interfere with sleep, while easy to handle and apply; and proper adhesion keeps the barrier patch in place, feels comfortable, and is easily removed.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating skin comprising:
   a) applying a cosmetic composition comprising an effective amount of a skin active agent to a target area of skin, and thereafter;
   b) applying a transparent barrier patch to the target area of skin, the barrier patch consisting of 3 layers and having a thickness of about 3 mils to about 15 mils, wherein
      (i) a first layer of the barrier patch is a polyethylene film backing layer comprising a first surface that is free of an effective amount of a skin active agent,
      (ii) a second layer of the barrier patch is a pressure sensitive acrylate adhesive layer in contact with the first surface of the backing layer, and
      (iii) a third layer of the barrier patch is a release layer comprising a film that covers a surface of the pressure sensitive adhesive opposite the backing layer; and
   c) adjusting the barrier patch to provide an adhesive release force of about 50 g to about 400 g, a Water Vapor Transmission Rate (WVTR) of about 1 $g/m^2/24$ h to about 20 $g/m^2/24$ h and a flexibility of about 10 g to about 25 g.

2. The method of claim 1 wherein the barrier patch is water impermeable.

3. The method of claim 1 wherein the pressure sensitive adhesive provides an adhesive release force from about 100 g to about 200 g.

4. The method of claim 1 wherein the barrier patch is free of an effective amount of a skin active agent.

5. The method of claim 1 wherein the barrier patch completely covers the cosmetic composition.

6. The method of claim 1 wherein the cosmetic composition and barrier patch remain in contact with the target area of skin for a period of time from about 4 hours to about 24 hours.

7. The method of claim 6 wherein the cosmetic composition and barrier patch remain in contact with the target area of skin for a period of time from about 5 hours to about 10 hours.

8. The method of claim 1 wherein the barrier patch is adjusted to provide a hydration value from about 35 to about 120.

9. The method of claim 1 further comprising step d) repeating steps a) to b) daily from about 2 weeks to about 12 weeks.

10. The method of claim 1 wherein the target area of the skin comprises from about 1 $cm^2$ to about 50 $cm^2$.

11. The method of claim 10 wherein the target area of the skin comprises from about 5 $cm^2$ to about 15 $cm^2$.

12. The method of claim 1 wherein the cosmetic composition comprises from about 0.01% to about 10% by weight of vitamin B.

13. The method of claim 12 wherein the cosmetic composition further comprises niacinamide, glycerine, tocopherol acetate, d-panthenol, or combinations thereof.

14. The method of claim 1 wherein the skin active agent comprises from about 0.01% to about 10% of a skin active agent selected from the group consisting of vitamin E, vitamin A, palmitoyl-lysine-threonine, palmitoyl-lysine-threonine-threonine-lysine-serine, N-undecyl-10-enoyl-L-phenylalanine, retinyl propionate, N-acetyl glucosamine, vitamin C, tretinoin, salicylic acid, benzoic acid, benzoyl peroxide, and combinations thereof.

15. The method of claim 1 wherein the target area of skin is the facial skin surface.

16. The method of claim 1 wherein the WVTR is from about 2 $g/m^2/24$ h to about 20 $g/m^2/24$ h.

17. The method of claim 1 wherein the cosmetic composition is an oil in water emulsion.

18. The method of claim 1 wherein the barrier patch is essentially free of a non-woven material.

19. The method of claim 1, wherein the release layer is paper coated with polyethylene and silicone.

\* \* \* \* \*